United States Patent [19]

Marple et al.

[11] Patent Number: 5,343,767
[45] Date of Patent: Sep. 6, 1994

[54] LOW PARTICLE LOSS CASCADE IMPACTOR

[75] Inventors: Virgil A. Marple, Maple Plain; Nicholas C. Miller, White Bear Lake, both of Minn.

[73] Assignee: MSP Corporation, Minneapolis, Minn.

[21] Appl. No.: 851,570

[22] Filed: Mar. 16, 1992

[51] Int. Cl.$^5$ .............................................. G01N 15/02
[52] U.S. Cl. ................................................. 73/863.22
[58] Field of Search ............... 73/28.05, 28.06, 863.22, 73/865.5; 55/270, 436, 444, 446, 466

[56] References Cited

U.S. PATENT DOCUMENTS

| | | | |
|---|---|---|---|
| 3,127,763 | 4/1964 | Lippmann | 73/28.06 |
| 3,938,366 | 2/1976 | Wertlake et al. | 73/28.06 |
| 4,133,202 | 1/1979 | Marple | 73/28 |
| 4,321,822 | 3/1982 | Marple et al. | 73/28 |
| 4,400,982 | 8/1983 | Bell | 73/863.22 |
| 4,670,135 | 6/1987 | Marple et al. | 509/143 |
| 4,767,524 | 8/1988 | Yeh et al. | 73/28.05 |
| 4,827,779 | 5/1989 | Marple et al. | 73/863 |
| 4,972,957 | 11/1990 | Liu et al. | 209/143 |

FOREIGN PATENT DOCUMENTS

| | | | |
|---|---|---|---|
| 2853615 | 6/1980 | Fed. Rep. of Germany | 73/863.22 |
| 0093929 | 5/1986 | Japan | 73/863.22 |

OTHER PUBLICATIONS

"The Twin Impinger: A Simple Device for Assessing the Delivery of Drugs from Metered Dose Pressurized Aerosol Inhalers," Hallworth et al, *J. Pharm. Pharmacol.*, 1987, 39, pp. 966–972.

"Stimuli to the Revision Process," Report and Recommendations of the USP Advisory Panel on Aerosols on the USP General Chapter (601) Aerosols, 1991, pp. 1703–1713.

*Primary Examiner*—Robert Raevis
*Attorney, Agent, or Firm*—Westman, Champlin & Kelly

[57] ABSTRACT

The present invention relates to a low particle loss cascade impactor with particle collection in externally removable cups for determining the size distribution of particles delivered form an aerosol atomizer. A plurality of downwardly facing cavities formed in the body are arranged from a first end to a second end of the body in a generally zig-zag pattern. Each cavity has a generally cylindrical inner wall surface defining an opening facing in a second direction and a surface facing in a first direction. An entrance passage extends from the outer surface of the body at the first end to a center region of a first cavity. The impaction stage is positioned such that a center line of the impaction stage intersects a center bisecting plane passing through the body at an included angle between about 10° to 80°. The body has a plurality of cavity passages which extend between adjacent cavities from the inner wall of one cavity adjacent the outlet opening of that cavity to a central region of the adjacent cavity. Nozzles are formed in the entrance passage and in each cavity passage. Part of the collection and impaction surfaces are provided adjacent to each cavity for the collection of particles. An airflow generator connected to the cavity next adjacent the second end of the body causes air to flow into the body at the entrance passage and flow through the plurality of cavities via the cavity passages.

14 Claims, 2 Drawing Sheets

LOW PARTICLE LOSS CASCADE IMPACTOR

BACKGROUND OF THE INVENTION

The present invention relates generally to particle impactors and, more particularly, to low particle loss cascade impactors with externally removable collection cups.

Cascade impactors have been used extensively for a number of years to determine the size distribution of aerosol particles. Generally, a cascade impactor has a plurality of collection stages arranged in series, each stage having a nozzle orifice decreasing in size over that of the previous stage and also having an impaction surface for the collection of the particles. The smaller the nozzle orifice, the higher the velocity of air or gas and particles moving through the orifice. The higher the velocity, the smaller the particles that are collected on the impaction plate.

Particles larger than the cut size of the impactor impinge upon the impaction plate. The cut size or cut point of the impactor is the point of 50% collection efficiency. The smaller particles pass with the air stream out of the first impaction region and proceed to the next stage. This procedure continues through the cascade impactor with each stage having higher velocity and collecting smaller size particles. Therefore, the particles collected on the various stages of the impactor will be larger than the cut size of that particular stage and less than the cut size of the stage preceding it. Often, cascade impactors will collect particles upon a flat plate and these particles are analyzed by weighing them and the plate and subtracting the tare weight of the plate. Alternatively, the amount of material deposited on the plate is determined by quantitative chemical analysis. With this latter technique, it would be desirable to collect particles directly into a container where the particles can be analyzed.

A second problem is that particles may be collected on surfaces other than the impaction plates. This is known as interstage particle loss. The reasons for interstage losses is that the airflow passing from one stage to the next must make a series of bends due to the shape of the impaction area and the shapes of the passages leading from one stage to the next stage. For example, in the conventional cascade impactor, the air impinges upon an impaction plate, traverses tangentially outward, and then proceeds downward into the next stage where the flow is directed toward the center and then downward through the nozzles in the next stage of the impactor. The result of these turns is the increased opportunity for the particles to be lost either by impaction or turbulent deposition.

SUMMARY OF THE INVENTION

The present invention relates to a low particle loss cascade impactor with particle collection in externally removable cups for determining the size distribution of aerosol particles carried in an airflow. The assembly includes a body having formed therein a plurality of downwardly facing cavities which are arranged from a first end to a second end of the body in a generally alternating zig-zag pattern from a center upright bisecting plane so that successive cavities alternate from one side to the other side of the center bisecting plane passing through the body. Each cavity has a generally cylindrical inner wall surface defining an opening facing in a second direction and a plate surface facing in a first direction (generally upwardly).

The body has an entrance passage having an inlet opening located at an outer surface near the first end of the body. The entrance passage extends from the outer surface of the body at the first end to a center region of a first or entrance cavity. The body has a plurality of cavity passages, each extending between adjacent cavities in a series flow path from the inner wall of one cavity adjacent an outlet opening from that cavity to a central region of the next adjacent downstream cavity. The airflow path leads from the entrance passageway through the series of cavity passages to an outlet.

To assure the proper function of the impaction surfaces each cavity passage may be positioned such that the center line of the respective cavity passage intersects the center bisecting plane passing through the body at an inclined angle facing in a second direction at any angle except those approaching 0° and 90°, for example, between 10° and 80° from the bisecting plane. Nozzles are formed in the entrance passage in each cavity passage. Particle collection is provided by separate impaction surfaces for the collection of particles impinging thereon from the entrance passage in each cavity passage. These impaction surfaces are formed in collection cups.

An airflow generator or pump is connected to the cavity next adjacent the second end of the body to cause air to flow into the body at the inlet opening of the entrance passage and flow through the plurality of cavities via the cavity passages.

DETAILED DESCRIPTION OF THE PREFERRED EMBODIMENTS

Figure 1:
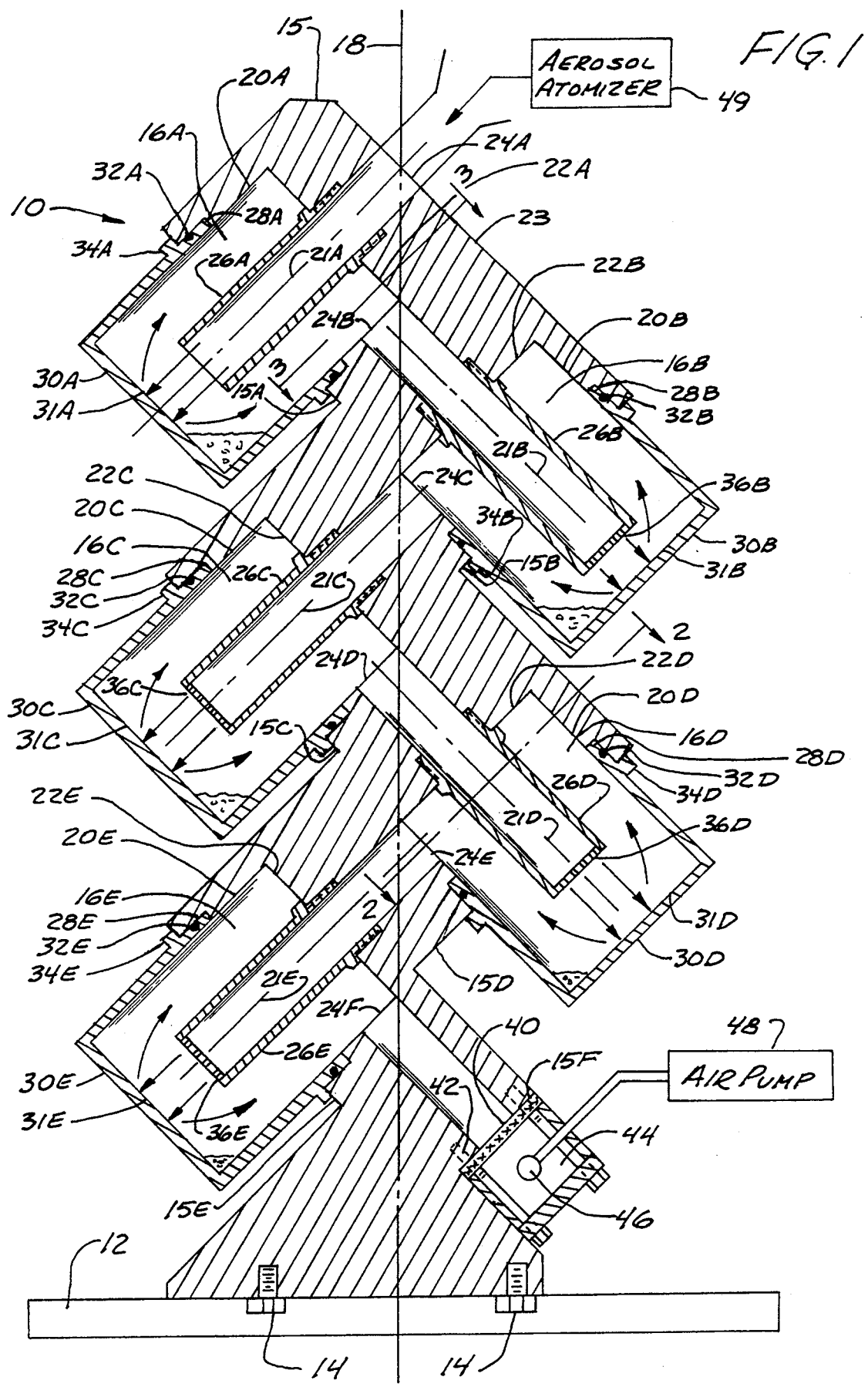
FIG. 1 is a vertical sectional view of a cascade impactor made according to the present invention.

As shown in FIG. 1, a cascade impactor assembly 10 mounts to a horizontal base plate 12 and is held firmly thereto by cap screws 14.

Figure 2:
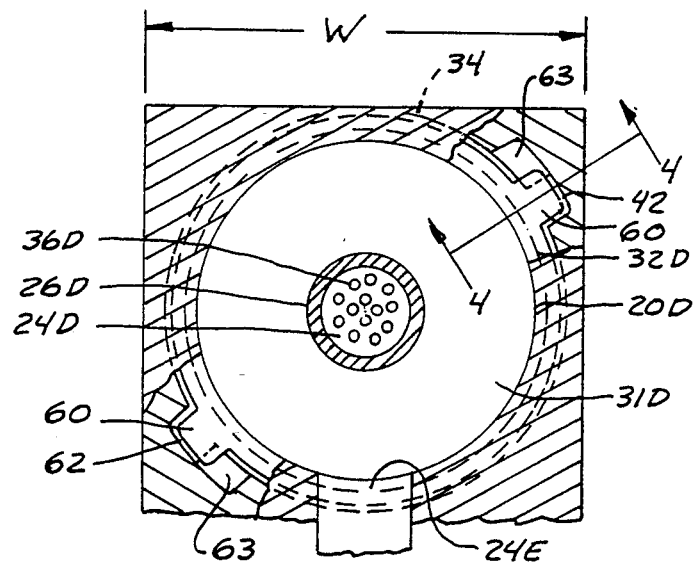
FIG. 2 is a sectional view taken on line 2—2 in FIG. 1 rotated 90° and with corners broken away to show twist lock grooves.

Cascade impactor 10 is made, as shown, of a solid block of material 15 that is initially rectangular in shape, and while this unit can be made in separate parts and assembled together, when a solid block of material 15 is utilized, a plurality of planar machine cuts are formed along surfaces 15A, 15B, 15C, 15D and 15E which are on the opposite side of a bisecting plane 18, as shown, and each is a planar cut that is formed at an included angle with respect to the plane 18. As shown in FIG. 2, for example, the block 15 is rectangular in shape with the width being shown as dimension W. These planar cuts, 15A and 15B, form surfaces that are downwardly facing. Further planar cuts are made and include cuts 15C, which is on the same side of the bisecting plane 18 as cut 15A and is parallel to cut 15A, and an additional cut 15D is provided on the opposite side of the plane from cut 15C and at a lower level, but is made parallel to, and on the same side of the bisecting plane as the machine cut 15B.

A lowermost cut is made at 15E, and this one is on the opposite side of the plane 18 from cut 15B, but is parallel to, and on the same side of the bisecting plane 18 as the cuts 15A and 15C.

A final machining cut shown at 15F is made adjacent the base portion 12, and as will be explained, it forms a seat for a filter, and a receptacle or cup that will be connected to an air pump.

Each of the surfaces 15A–15E of cascade impactor assembly 10 has a downwardly facing cavity 16A, 16B, 16C, 16D and 16E respectively, formed therein with axes perpendicular to the respective surfaces 15A–15E. The cavities 16A–16E are thus arranged from a top end of cascade impactor assembly 10 toward base plate 12 in a generally alternating zig-zag pattern such that successive adjacent cavities alternate from one side to the other side of center bisecting plane 18. The central axes of the cavities 16A–16E, as shown, are positioned at a 45° angle to the plane 18.

The bores forming the cavities 16A, 16B, 16C, 16D and 16E each have a cylindrical inner wall surface 20A, 20B, 20C, 20D and 20E, respectively, defining an opening at each of the respective machined faces 15A–15E. The openings 16A–16E face in direction generally toward base plate 12. Each of the bores forming the cavities 16A–16E has a central axis shown at 21A–21E, that are perpendicular to the respective surfaces 15A–15E. Block 15 also has a surface 23 at its upper end which is parallel to the surfaces 15A, 15C, and 15E. This provides an upper inlet end surface.

Each of the bores forming cavities 16A–16E has a substantially planar inner end surface indicated at 22A–22E, respectively, and these inner end surfaces 22A–22E are parallel to the respective machined surface 15A–15E, but are spaced inwardly in the block therefrom to form the recess for the bore.

The bore forming cavity 16A has an opening 24A at its inner end, which is centered on the axis 21A, and which extends to the inlet end outer surface 23. The bore 24A is recessed slightly at its inner end adjacent the surface 22A, and supports a nozzle tube 26A that projects into the bore and is concentric therewith. The cavity 16A also has a counter recess or bore 28A at its outer end and an impactor plate cup indicated at 30A with impactor surface 31A, is slid into this counter bore. The cup 30A has a recess for an O-ring 32A which forms a sealing friction fit on the bore 28A and includes a stop flange 34A that limits the amount of penetration of the cup 30A and properly positions the cup in its desired location. The cups can be held in position with a twist lock or bayonet lock arrangement wherein the cup has a pair of ears that fit into slots and when seated and twisted, the ears are latched into a recessed groove as will be shown.

The axis 21A and, thus, the angle of the nozzle tube is the same as the inclination of the cavity 16A, and it can be seen that the cup 30A is concentric with the axis 21A, as well.

Figure 3:
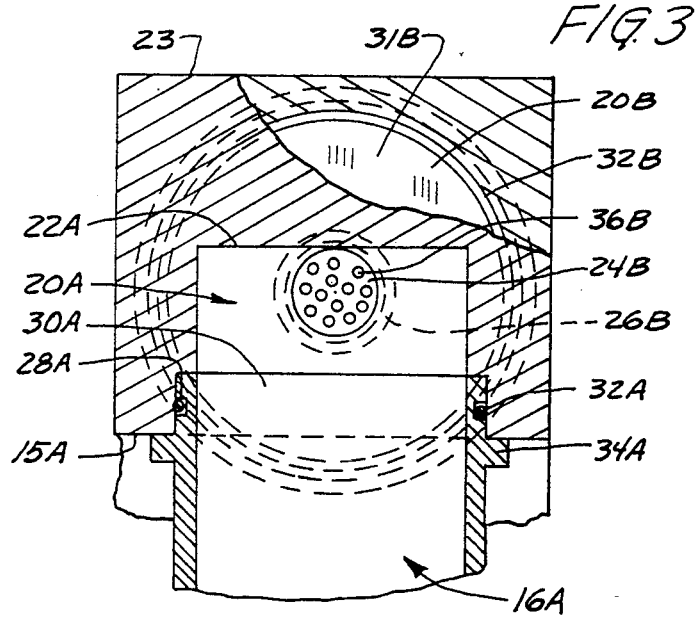
FIG. 3 is a sectional view taken on line 3—3 in FIG. 1 and rotated 90°.

The inner end of the bore forming the cavity 16A has a further cylindrical bore 24B opening from the cavity and centered on the axis 21B. Bore or passageway 24B opens to the interior of the cavity 16A and, thus, to the interior of the cup 30A. The bore 24B extends into the cavity 16B. The bore 24B is tangent to surface 22A, as shown typically in FIG. 3. Axis 21B is thus parallel to the plane of surface 22A. The bore 24B has a recess at its end adjacent cavity 16B that is threaded or otherwise prepared to receive a nozzle tube 26B that projects concentrically with the cavity 16B. The nozzle tube 26B extends outwardly beyond the plane of the machined surface 15B (the nozzle tube 26A also projects out beyond the plane of surface 15A) and nozzle tube 16B has an end nozzle plate 36B that has a selected number of openings, as shown, for example 10 openings.

The bore forming the cavity 16B is recessed as at 28B and receives an upper end of a cup 30B that has an end wall forming an impactor surface or plate 31B. The upper end of the cup 30B has a recess receiving an O-ring 32B that forms a sealing friction fit in the counterbore 28B. The cup 30B has a flange or stop 34B to properly position the cup.

The bore 24B and nozzle 26B form an airflow passage from the first cavity 16A and first impactor cup 30A to the second impactor cup 30B.

A third bore 24C is adjacent to and tangent with the surface 22B, and concentric with the axis 21C. The third bore 24C opens to the bore forming the cavity 16B. The bore 24C opens to the surface 22C, and is concentric with the bore forming the cavity 16C. The end of the bore 24C, adjacent the surface 22C, is counterbored and threaded to receive a nozzle 26C that projects concentric outwardly beyond the plane of surface 15C. A nozzle plate 36C is provided at the end of the nozzle 26C. Nozzle plate 36C has a greater number of openings than the nozzle plate 36B, for example 20 openings forming smaller nozzles with a smaller total open area.

The cavity 16C is counterbored as at 28C at its outer end and an impactor plate cup 30C is slipped into the counterbore. The cup sidewall has a recess receiving an O-ring 32C at its outer end, and the O-ring provides a sealing friction fit when the outer end of the cup 30C is slid into the counterbore 28C. The cup 30C has a flange 34C for retaining it in position against the surface 15C. At the end of the cavity 16C adjacent the surface 15C, a further airflow bore 24D is formed, which opens to the surface 22D. The bore 24D is cylindrical and tangent with the surface 22C, and has its end counterbored to receive a nozzle tube 26D. The nozzle tube 26D projects outwardly beyond the plane of the surface 15D, and has a nozzle plate 36D at its outer end. An impactor cup 30D is provided and held in a counterbore 28D at the outer end of the cavity 16D. The upper end of the impactor cup 30D has a recess for receiving an O-ring 32D that sealingly fits on the inside surfaces of the counterbore 28D. The impactor cup also has a stop flange or surface 34D to properly position the cup when it is locked in working position.

Figure 4:
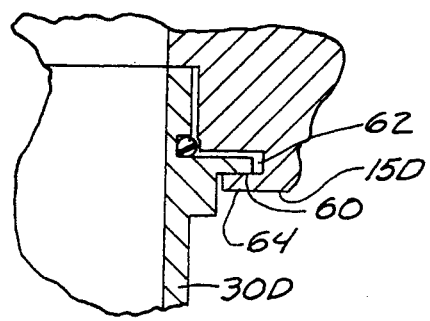
FIG. 4 is a fragmentary sectional view taken on line 4—4 in FIG. 2.

The cup holding twist lock arrangement is shown in FIGS. 2 and 4. The cups each have a pair of ears 60 that extend outwardly. The lock grooves 62 are provided in each surface 15 with an opening 63 to permit the ears 40 to slip into the groove and then by twisting the respective cup, the ears rest above a wall 64 to hold the cup in position.

An air passage bore 24E is provided concentric with the axis 21E, and opens to the cavity 16D, and, thus, to the impactor cup 30D. The bore 24E also opens into cavity 16E through surface 22E and is recessed at its end adjacent cavity 16E and is threaded to receive a nozzle tube 26E. The nozzle tube 26E projects outwardly beyond the plane of surface 15E and has a nozzle plate 36E at its outer end with a larger number of openings than in the nozzle plate 36D. For example, nozzle plate 36E may have 80 openings of smaller size than the openings in nozzle plate 36D.

The cavity 16E has a counterbore 28E at its outer end and the counterbore is to receive an impactor cup 30E that has an impactor end plate forming an impactor surface 31E at its closed end, and which has an O-ring recess to receive an O-ring 32E to provide a friction seal in the counterbore 28E. A flange or stop 34E is also provided to properly position the impactor cup 30E in alignment with the end of nozzle tube 26E. The impactor cups can be retained in place with a twist lock arrangement as shown. Other latches for holding the cups retained in position can be used.

A bore 24F is formed in the block 15 at right angles to an axis 21E and perpendicular to the surface 15F. Bore 24F forms an outlet for airflow from the impactor. A filter 40 is shown supported to cover the outlet end of the opening 24F, and mounts against the surface 15F. The filter 40 can be held in with suitable cap screws 42, which also hold a cup shaped plenum 44. The plenum 44 has an outlet opening 46 that leads to an air pump 48 that generates an airflow through the impactor.

The purpose for using multiple nozzle plates 36 on the end of the nozzle tubes 26 is to keep overall system pressure low and initial air velocity low. Utilizing nozzle plates 36 with small openings as the air gets further down the system, the air is accelerated as it passes through the smaller openings, thus reaching a desired impaction speed. Without using multiple nozzles, the overall pressure drop of the system would have to be very high to maintain the desired impaction air speed.

When the air pump 48 is operating, air will flow at a known rate, for example, between 15 to 120 liters per minute, and at the inlet end surface 23, air carrying particles from a source such as an aerosol atomizer 49 will flow into the bore 24A through the nozzle tube 26A and will flow and impinge against the impactor surface 31A of the end plate of cup 30A. The surface 31A forms an impactor surface with cut size approximately 10 $\mu$, so large particles will be separated out as the air flows out of nozzle tube 26A and strikes the impaction surface 31A. After impaction, the air flows around the nozzle tube 26A toward the bore 24B, which forms the outlet from the cup 30A and cavity 16A. This air will flow through the nozzle tube 26B and will be accelerated as it passes through the plate 36B, which has ten openings of smaller total size than the cross section of the nozzle tube. Larger particles will be separated out by impaction in cup 30A so the openings in plate 36B can be of smaller size without trapping the particles. Particles of a selected size will then impinge against the impactor surface 31B with a cut size of approximately 5 $\mu$, at the closed end of the cup 30B. After impaction the air flows, as shown by the arrows, around the nozzle tube 26B and out through passageway or bore 24C. The air flow coming into the bore 24C will go down through the nozzle tube 26C and out through the nozzle plate openings 36C (which are smaller than the openings in nozzle plate 36B). Further particles will impinge on the impactor surface 31C, with a cut size of approximately 2.5 $\mu$, at the closed end of the cup 30C. After impaction, the air flows around the nozzle tube 26C, and passes out through the bore 24D into the nozzle tube 26D. Nozzle plate 36D, which has a plurality of smaller openings causes some air acceleration, and air will flow through these openings into the cup 30D. Particles will impinge on the impactor surface 31D, which has a cut size of approximately 1.25 $\mu$. The air will then flow up around the cavity 16D and out through the bore 24E into the nozzle tube 26E. This air flow will pass through the nozzle plate 36E, which may have as many as 80 openings, because the larger particles will have been removed in prior stages in the prior impactor cups. The air will impinge on the surface 31E, having a cut size of approximately 0.625 $\mu$. Substantial quantities of particles in the air will have been removed by that time through the series of impactors because of the particle cut off size selection. The air will flow around the nozzle tube 26E and out the bore 24F, through the filter, into the plenum cup 44, and then out through the air pump 48.

Each of the cups 30A-30E has a generally circular base, as shown, forming the impactor plate having a surface perpendicular to the axis of the nozzles.

The pattern of air flow ensures very low particle loss against side walls of the cup 50E.

The cups and contents can then be analyzed for determining the particle size distribution without loss of particles. The low loss is particularly important when analyzing atomizers for atomizing liquid drops of material that form the particles. This device is thus especially suited for use with atomized particles of liquid as well as being useful for other aerosols. The cups ensure that all particles or aerosols are collected accurately. The air flow is smooth and the number of changes of direction of air flow is reduced. The angled orientation of the impactor cups relative to the upright bisecting plane permits a compact unit with efficient operation and complete collection of the aerosols.

The cups 30A-30E are all positioned on an exterior, readily accessible surface so each of the cups can be removed and reinserted without disturbing any other cups. The zig-zag or alternating surfaces which have the recesses for the cups are exposed to the exterior of the unit for such access.

Although the present invention has been described with reference to preferred embodiments, workers skilled in the art will recognize that changes may be made in form and detail without departing from the spirit and scope of the invention.

What is claimed is:

1. A low particle cascade impactor assembly for determining the size distribution of particles delivered from a source, comprising:

a body having formed therein a plurality of at least three downwardly facing cavities which are arranged from a first end to a second end of the body in a generally zig-zag pattern, each cavity having a wall surface formed around a central axis and encompassing the cavity and defining an opening facing in a second direction, and each cavity having an outlet opening through the encompassing wall;

the body having an entrance passage having an inlet opening located at an outer surface adjacent the first end, the entrance passage extending from the outer surface of the body at the first end to a central region of a first cavity;

a plurality of cavity passages in the body, each cavity passage extending between adjacent cavities from an outlet opening of the encompassing inner wall of one cavity to a central region of the adjacent cavity positioned in a direction toward the second end of the body;

nozzle means formed in the entrance passage and each cavity passage;

a separate particle collection cup associated with each cavity and having an end wall to provide a separate impaction surface for the collection of particles impinging thereon from the respective nozzle means, the nozzle means each comprising an elongated tube extending into the associated cup in a direction along the respective central axis and having a discharge end adjacent the end wall of the associated cup; and air flow generator means connected to the cavity adjacent the second end of the body to cause air to flow into the body at the inlet opening of the entrance passage, and in series through the nozzle means and plurality of cavities and cavity passages.

2. The apparatus of claim 1 wherein the source is an aerosol atomizer.

3. The apparatus of claim 1 wherein the plurality of cavities alternate from side to side of a central vertical bisecting plane passing through the body, the central axes of the cavities being positioned at angles from the vertical bisecting plane of between 10° and 80°.

4. The apparatus of claim 1 wherein the impaction surface of each cup is perpendicular to the central axis of the respective cavity.

5. The apparatus of claim 1 wherein each cavity passage has a recess at an inner end, of size to receive the nozzle means.

6. The apparatus of claim 5 wherein the recess is threaded to receive nozzle means.

7. The apparatus of claim 1 wherein the particle collection cups have a generally circular base with a generally cylindrical wall attached thereto, the cylindrical wall having an outer surface.

8. The apparatus of claim 7 wherein each cup has an annular groove formed in an upper region of the outer surface of the cylindrical wall, an o-ring positioned in the groove for forming a friction fit and seal between the wall surface of the associated cavity and the cylindrical wall of the respective cup when such cup is inserted into the associated cavity.

9. A low particle loss cascade impactor assembly for determining the size distribution of particles delivered from a source, comprising:

a body having formed therein a plurality of exposed surfaces spaced along a longitudinal axis and the exposed surfaces being at acute angels relative to the longitudinal axis;

a removable particle collection cup mounted on the body relative to each surface and having an end wall to provide a separate impaction surface in the cup for the collection of particles impinging thereon;

airflow passage means formed in the body connecting an inlet opening to a first exposed surface and connecting each cup in series flow to the next exposed surface along the longitudinal axis and the associated cup, and then to an outlet; and a separate nozzle forming part of the air flow passage means leading to each cup for directing air flow toward and substantially perpendicular to the impaction surface of the particle collecting cup associated with each respective exposed surface, the nozzle discharging adjacent the impaction surface, the air flow passage means forming an outlet from the cup spaced from the impaction surface, a wall including at least a portion of the cup surrounding the nozzle such that air flow from the nozzle reverses direction and flows around an exterior of the nozzle as the flow moves to the outlet from the respective cup to the next cup, each cup being directly removable from the body at the exterior of the body.

10. The impactor assembly of claim 9 wherein the exposed surfaces are arranged alternately on opposite sides of a bisecting plane passing through the longitudinal axis.

11. The impactor assembly of claim 9 wherein the nozzle comprises an elongated tube positioned generally along a central axis of the respective cup, the wall surrounding the nozzle forming an air flow passage of larger cross-sectional flow area than the nozzle leading to the outlet from the respective cup.

12. The impactor assembly of claim 10 wherein the cup associated with each exposed surface extends at an acute angle relative to the bisecting plane, and each cup on the same side of the bisecting plane is spaced along the longitudinal axis from adjacent cups.

13. The impactor assembly of claim 9 wherein the longitudinal axis of the body extends substantially vertically, and the inlet opening is adjacent an upper end of the body, and the flow path leads to an outlet from the body adjacent a lower end thereof.

14. The impactor assembly of claim 9 wherein each nozzle comprises an elongated tube extending from the respective exposed surface, a tube connected to each respective exposed surface is of substantially the same cross-sectional size, and a plate at the end of the tube adjacent the respective impaction surface on at least the tubes forming nozzles subsequent to the nozzle leading from the inlet, the plates having selected size openings for controlling flow through the respective nozzles.

* * * * *

UNITED STATES PATENT AND TRADEMARK OFFICE
CERTIFICATE OF CORRECTION

PATENT NO. : 5,343,767
DATED : September 6, 1994
INVENTOR(S) : Virgil A. Marple and
Nicholas C. Miller It is certified that error appears in the above-indentified patent and that said Letters Patent is hereby corrected as shown below:

Column 6, Line 42 (Claim 1, line 1), before "cascade" insert --loss--

Signed and Sealed this

Thirteenth Day of December, 1994

Attest:

BRUCE LEHMAN

Attesting Officer    Commissioner of Patents and Trademarks